United States Patent
Chen et al.

(10) Patent No.: US 7,989,770 B2
(45) Date of Patent: Aug. 2, 2011

(54) CONTROL UNIT AND CONTROL METHOD FOR RADIATION SOURCE AND RADIATION INSPECTION SYSTEM AND METHOD THEREOF

(75) Inventors: Zhiqiang Chen, Beijing (CN); Yuanjing Li, Beijing (CN); Yinong Liu, Beijing (CN); Junli Li, Beijing (CN); Hua Peng, Beijing (CN); Yaohong Liu, Beijing (CN); Shangmin Sun, Beijing (CN); Jinyu Zhang, Beijing (CN); Qingjun Zhang, Beijing (CN); Li Zhang, Beijing (CN); Yali Xie, Beijing (CN); Yanli Deng, Beijing (CN); Ming Ruan, Beijing (CN); Siyuan Liang, Beijing (CN); Guang Yang, Beijing (CN); Wei Jia, Beijing (CN)

(73) Assignees: Nuctech Company Limited, Beijing (CN); Tsinghua University, Beijing, P.A. (CN)

( * ) Notice: Subject to any disclaimer, the term of this patent is extended or adjusted under 35 U.S.C. 154(b) by 409 days.

(21) Appl. No.: 11/997,454
(22) PCT Filed: Dec. 22, 2006
(86) PCT No.: PCT/CN2006/003550
§ 371 (c)(1), (2), (4) Date: Feb. 27, 2008
(87) PCT Pub. No.: WO2008/052395
PCT Pub. Date: May 8, 2008

(65) Prior Publication Data
US 2009/0065698 A1    Mar. 12, 2009

(30) Foreign Application Priority Data
Oct. 13, 2006   (CN) .......................... 2006 1 0113717

(51) Int. Cl.
*G01J 1/42*   (2006.01)
*G01T 1/00*   (2006.01)

(52) U.S. Cl. ............... 250/354.1; 250/358.1; 250/359.1; 250/360.1
(58) Field of Classification Search ............... 250/360.1, 250/354.1
See application file for complete search history.

(56) References Cited

U.S. PATENT DOCUMENTS
4,430,568 A   2/1984   Yoshida et al. ............ 250/358.1
(Continued)

FOREIGN PATENT DOCUMENTS
CN   1295248 A   5/2001
(Continued)

OTHER PUBLICATIONS

English translation of written opinion for PCT/CN2006/003550, 4 pages.*

(Continued)

*Primary Examiner* — David P Porta
*Assistant Examiner* — Carolyn Igyarto
(74) *Attorney, Agent, or Firm* — Westman, Champlin & Kelly, P.A.

(57) ABSTRACT

A radiation inspection system is disclosed. The radiation inspection system comprises: an inspection passage through which a moving object under inspection can pass, a radiation source disposed on a side of the inspection passage for emitting radiation, an array of detectors disposed on the other side of the inspection passage opposite to the radiation source for receiving the radiation emitted from the radiation source, a detector for detecting the moving object, and a controller for receiving a signal from the detector and controlling the radiation source to emit radiation when the detector detects the moving object for radiation imaging and inspection of the moving object. According to the radiation inspection system, the controller can control the radiation source to automatically emit radiation beam based on the detection signal from the detector for inspecting the moving object. As a result, inspection efficiency is improved, safety is increased, and misoperation of the radiation source is eliminated.

32 Claims, 2 Drawing Sheets

U.S. PATENT DOCUMENTS

| | | |
|---|---|---|
| 6,031,890 A | 2/2000 | Bermbach et al. ............... 378/57 |
| 6,529,008 B1 | 3/2003 | Mohamed ..................... 324/345 |
| 7,039,159 B2 | 5/2006 | Muenchau et al. .............. 378/57 |
| 7,045,787 B1 | 5/2006 | Verbinski et al. ........... 250/358.1 |
| 2004/0179647 A1* | 9/2004 | Zhao et al. ...................... 378/57 |
| 2005/0169421 A1 | 8/2005 | Muenchau et al. .............. 378/57 |

FOREIGN PATENT DOCUMENTS

| | | |
|---|---|---|
| CN | 1333462 A | 1/2002 |
| CN | 1743836 A | 3/2006 |
| JP | 08-178872 | 7/1996 |
| JP | 11-339138 | 7/1996 |
| JP | 10105870 | 4/1998 |
| JP | 2004534219 | 11/2004 |
| JP | 2005309671 | 11/2004 |

OTHER PUBLICATIONS

International Search Report for PCT/CN2006/003550, 4 pages.
Written opinion for PCT/CN2006/003550, 4 pages.

* cited by examiner

CONTROL UNIT AND CONTROL METHOD FOR RADIATION SOURCE AND RADIATION INSPECTION SYSTEM AND METHOD THEREOF

CROSS-REFERENCE TO RELATED APPLICATION

This Application is a Section 371 National Stage Application of International Application No. PCT/CN2006/003550, filed Dec. 22, 2006 not yet published, the content of which is hereby incorporated by reference in its entirety.

BACKGROUND OF THE INVENTION

1. Field of the Invention

The present invention relates to a control unit and a control method for controlling a radiation source to automatically emit a radiation beam, and a radiation inspection system and a radiation inspection method for automatically imaging moving objects by means of radiation.

2. Description of the Related Art

In a system for quickly inspecting a moving object such as a vehicle by means of high energy rays, generally, a driver drives a vehicle under inspection to pass through a radiation beam flux plane. Specifically, after a cab of the vehicle moves across the radiation beam flux plane, the driver stops the vehicle. Then, a button is manually pressed so that a radiation source is controlled to emit a radiation beam. Next, the driver starts the vehicle again to drive the vehicle under inspection to pass through the radiation beam flux plane so that a moving object such as a vehicle is scanned to be imaged. However, the entire inspection process takes about one minute so that the system is low in vehicle inspection efficiency.

SUMMARY OF THE INVENTION

In order to overcome at least one aspect of the above defects existing in the prior art, it is an object of the present invention to provide a unit and a method for controlling a radiation source to automatically emit a radiation beam as well as an inspection system and an imaging method for controlling a radiation source to automatically emit a radiation beam, which can greatly improve a passing rate of a vehicle.

The control unit and method thereof as well as the inspection system and method thereof can automatically control the radiation source to emit a radiation beam so as to carry out scanning, automatic imaging and inspection. A vehicle can be automatically inspected while it is running. It is not necessary for a driver to stop the vehicle and press a button to start the radiation source to emit a radiation beam, and then to start the vehicle again to carry out scanning. As a result, the inspection time can be greatly shortened so that a passing rate of a vehicle and an inspection rate can be improved.

In order to achieve at least one object of the present invention, in accordance with an aspect of the present invention, there is provided a control unit for a radiation source, the radiation source being operable to emit radiation for radiation inspection of a moving object passing through an inspection passage. The control unit comprises: a first detector disposed downstream of the radiation source in an advancing direction of the moving object and spaced from the radiation source by a predetermined distance to detect the moving object passing through the inspection passage, and a controller for receiving a signal from the first detector and controlling the radiation source to automatically emit radiation when the first detector detects the moving object.

Preferably, the control unit further comprises a second detector disposed under the ground surface of the inspection passage upstream of the first detector in the advancing direction of the moving object, wherein only when both the first detector and the second detector detect the moving object, the controller controls the radiation source to automatically emit the radiation.

Alternatively, the control unit further comprises a third detector disposed upstream of the second detector in the advancing direction of the moving object, wherein only when all the third detector, the first detector and the second detector detect the moving object in sequence, the controller controls the radiation source to automatically emit the radiation.

In addition, the control unit further comprises a fourth detector disposed upstream of the third detector in the advancing direction of the moving object, wherein only when all the fourth detector, the third detector, the first detector and the second detector detect the moving object in sequence, the controller controls the radiation source to automatically emit the radiation.

In accordance with a second aspect of the present invention, there is provided a method of controlling a radiation source, the radiation source being operable to emit radiation for inspecting of a moving object passing through an inspection passage. The method comprises steps of providing a first detector downstream of the radiation source in an advancing direction of the moving object at a predetermined distance from the radiation source, providing a controller for receiving a signal from the first detector to control the radiation source, and controlling the radiation source by the controller to automatically emit radiation when the first detector detects the moving object.

In accordance with a third aspect of the present invention, there is provided a radiation inspection system comprising an inspection passage through which a moving object under inspection can pass, a radiation source disposed on a side of the inspection passage for emitting radiation, an array of detectors disposed on the other side of the inspection passage opposite to the radiation source for receiving the radiation emitted from the radiation source, a first detector disposed downstream of the radiation source in an advancing direction of the moving object and spaced from the radiation source by a predetermined distance to detect the moving object, and a controller for receiving a signal from the first detector and controlling the radiation source to emit radiation when the first detector detects the moving object for radiation imaging and inspection of the moving object.

In accordance with a fourth aspect of the present invention, there is provided a method of inspecting a moving object with radiation comprising the steps of: providing an inspection passage through which the moving object under inspection passes, providing a radiation source on a side of the inspection passage for emitting radiation, providing an array of detectors on the other side of the inspection passage opposite to the radiation source for receiving the radiation emitted from the radiation source, providing a first detector downstream of the radiation source in an advancing direction of the moving object at a predetermined distance from the radiation source, providing a controller for receiving a signal from the first detector so as to control the radiation source, and controlling the radiation source by the controller to automatically emit radiation when the first detector detects the moving object.

With the present invention, the passing rate of vehicles under inspection can be improved to more than 200 container lorries per hour. The present invention can greatly improve vehicle inspection rate with high security and high efficiency so as to be applicable to various situations.

BRIEF DESCRIPTION OF THE DRAWINGS

These and/or other aspects and advantages of the present invention will become apparent and more readily appreciated from the following description of the embodiments, taken in conjunction with the accompanying drawing.

DETAILED DESCRIPTION OF THE EMBODIMENTS

Figure 1:
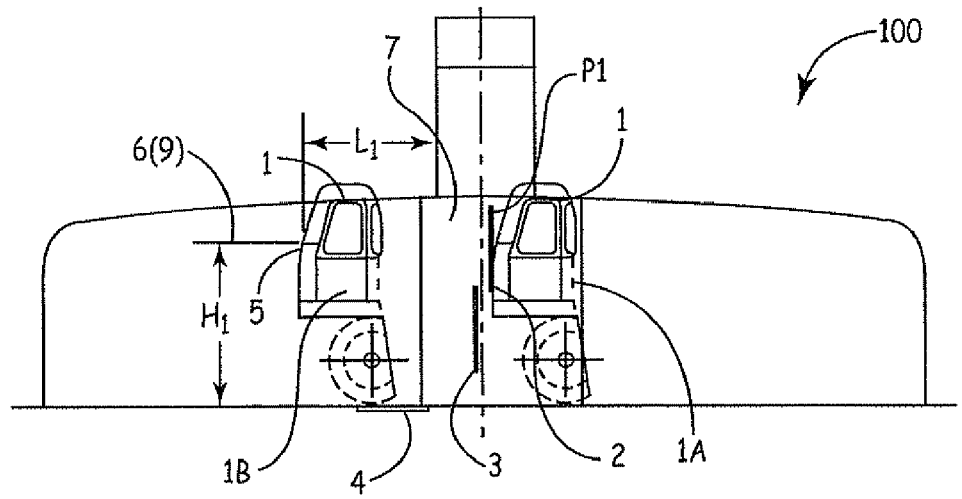
FIG. 1 is a schematic side view showing a control unit for controlling a radiation source to automatically emit a radiation beam according to an embodiment of the present invention.

Reference will now be made in detail to the embodiments of the present invention, examples of which are illustrated in the accompanying drawings, wherein like reference numerals refer to the like elements throughout. The embodiments are described below in order to explain the present invention by referring to the figures.

Figure 2:
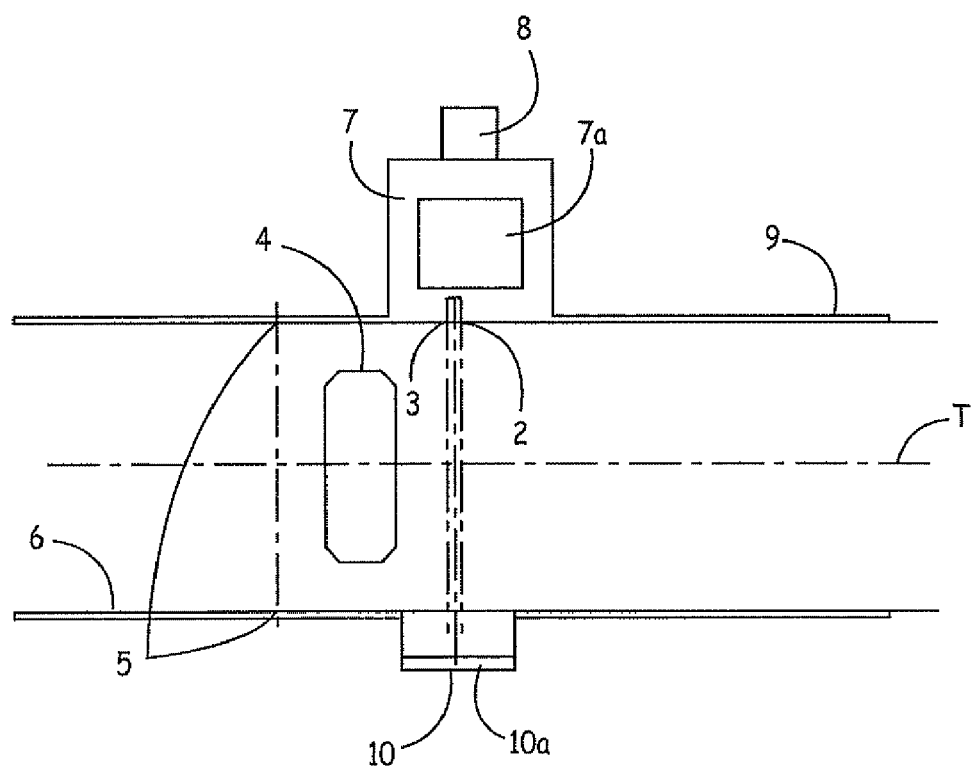
FIG. 2 is a schematic top view showing the control unit for controlling the radiation source to automatically emit a radiation beam according to the embodiment of the present invention.

FIGS. 1 and 2 show schematic side and top views of a control unit 100 for controlling a radiation source 7a to automatically emit a radiation beam according to an embodiment of the present invention, respectively. The radiation source 7a is used to emit radiation for inspecting a moving object 1 passing through an inspection passage T. The moving object 1, for example, may comprise a vehicle to be inspected carrying a container. The inspection passage T is composed of a first shielding wall 6 and a second shielding wall 9 which are substantially parallel to each other and spaced from each other.

As shown in FIG. 2, the radiation source 7a mounted in a radiation source housing 7 is disposed on a side of the inspection passage T and a detector arm 10 is disposed on the other side of the inspection passage T opposite to the radiation source 7a. The detector arm 10 is provided thereon with an array of detector 10a for receiving the radiation emitted from the radiation source 7a, which will be described in detail.

The control unit 100 comprises a photoelectric switch 5 as a first detector. The photoelectric switch 5 is used for detecting a vehicle 1 passing through the passage T to be inspected and may be disposed, for example, within the inspection passage T. Those skilled in the art can comprehend that the first detector is not limited to The photoelectric switch 5, but may comprise any appropriate sensors known to the art, for example.

The control unit 100 further comprises a controller 8 for receiving a signal from The photoelectric switch 5. The photoelectric switch 5 transmits a signal (a positive signal) that a vehicle 1 under inspection is detected to the controller 8 when The photoelectric switch 5 detects the vehicle 1 under inspection, so that the controller 8 controls the radiation source 7a to automatically emit radiation for radiation inspection of the vehicle 1. When The photoelectric switch 5 does not detect a vehicle 1 under inspection, the photoelectric switch 5 transmits a signal (a negative signal) that the vehicle 1 under inspection is not detected to the controller 8, so that the controller 8 controls the radiation source 7a not to automatically emit radiation.

Specifically, the photoelectric switch 5 is disposed downstream of the radiation source 7a in a advancing direction (towards left sides in FIGS. 1 and 2) of the vehicle 1 under inspection at a predetermined distance L1 from a radiation beam flux plane P1. The predetermined distance L1 is set in such a manner that a cab of the vehicle 1 under inspection passes through the radiation beam flux plane P1 and a container on the vehicle 1 under inspection is still located upstream (on right sides in FIGS. 1 and 2) of the radiation beam flux plane P1 so that before the cab passes through the radiation beam flux plane P1, the photoelectric switch 5 can not detect the vehicle 1 under inspection so that the photoelectric switch 5 does not send a positive signal to the controller 8, but send a negative signal to the controller 8. As a result, the controller 8 controls the radiation source 7a not to automatically emit radiation so as to ensure safety of a driver.

Preferably, the photoelectric switch 5 is disposed on the shielding wall 6 and/or the shielding wall 9 of the inspection passage T at a predetermined height H1 from the ground surface so that the photoelectric switch 5 can detect only moving objects passing through the inspection passage T which have a height greater than the predetermined height H1. For example, since the vehicle 1 under inspection has a height greater than the predetermined height H1, when the vehicle 1 under inspection passes through the passage T, the photoelectric switch 5 can detect the vehicle 1 to send a positive signal to the controller 8, so that the controller 8 controls the radiation source 7a to automatically emit radiation. When a person or other small vehicles with a height smaller than the predetermined height H1 pass through the inspection passage T, since the photoelectric switch 5 can not detect her/him or them, the photoelectric switch 5 sends a negative signal to the controller 8. As a result, the controller 8 controls the radiation source 7a not to automatically emit radiation so as to ensure safety and to avoid misoperation.

Preferably, the control unit 100 further comprises a ground surface induction coil sensor 4 as a second detector. The ground induction coil sensor 4 is disposed under the ground surface within the inspection passage T between the photoelectric switch 5 and the radiation beam flux plane P1 of the radiation source 7a. A person having ordinary skill in the art can understand that the second detector is not limited to the ground induction coil sensor 4, but may comprise any appropriate sensors known to the art.

When the vehicle 1 under inspection is driven to an outlet side (the left sides in FIGS. 1 and 2) from an inlet side (the right sides in FIGS. 1 and 2) of the inspection passage T, the vehicle 1 is first detected by the ground induction coil sensor 4 and then the cab at a front portion of the vehicle 1 under inspection is detected by the photoelectric switch 5. When the cab at a front portion of the vehicle 1 under inspection is detected by the photoelectric switch 5, a rear portion of the vehicle 1 under inspection has not passed through the radiation beam flux plane P1. When both the ground induction coil sensor 4 and the photoelectric switch 5 detects the vehicle 1 under inspection in sequence, they send positive signals to the controller 8 in sequence, so that the controller 8 controls the radiation source 7a to automatically emit radiation for scanning the vehicle 1 under inspection by radiation.

It should be noted that in accordance with characteristics of the ground induction coil sensor 4, only when a moving object moving within the inspection passage T overlaps or contacts the ground induction coil sensor 4 by an area of a certain degree, the ground induction coil sensor 4 sends a signal (a positive signal) that a moving object is detected to the controller 8 so as to further ensure safety of a driver and an operator. For example, when a person or other small vehicles pass through the inspection passage T, even if he/she or they move across the ground induction coil sensor 4, since he/she or they overlap or contact the ground induction coil sensor 4 by a small area, the ground induction coil sensor 4 can not send the positive signal to the controller 8, but sends a negative signal to the controller 8. Therefore, even if the photoelectric switch 5 can detect the vehicle 1, the controller 8 controls the radiation source 7a not to automatically emit radiation so as to avoid misoperation of the radiation source 7a. As a result, the control unit ensures that only predetermined moving objects passing through the inspection passage T are scanned by radiation so as to improve safety of the control unit.

In accordance with a further preferable embodiment, the control unit 100 further comprises a light curtain sensor 3 as a third detector. The light curtain sensor 3 is disposed within the inspection passage T between the ground induction coil sensor 4 and the radiation beam flux plane P1. Those skilled in the art can comprehend that the third detector is not limited to the light curtain sensor 3, but may, for example, comprise any appropriate sensors known to the art.

The light curtain sensor 3 not only can detect presence of a moving object, but also can identify a specific moving object, for example, type and the like of the vehicle 1, by imaging the moving object, so as to send a positive signal to the controller 8. As a result, the controller 8 controls the radiation source 7a to automatically emit radiation.

Specifically, in an example of the present invention, only when all the light curtain sensor 3, the ground induction coil sensor 4, and the photoelectric switch 5 detect the vehicle 1 under inspection in sequence so that they all send positive signals to the controller 8 in sequence, the controller 8 controls the radiation source 7a to automatically emit radiation. If anyone of the light curtain sensor 3, the ground induction coil sensor 4, and the photoelectric switch 5 does not send a positive signal to the controller 8, the controller 8 controls the radiation source 7a not to automatically emit radiation, so as to improve the safety and reliably avoid the misoperation of the radiation source 7a.

In accordance with a still further preferable embodiment, the control unit 100 further comprises a light curtain sensor 2 as a fourth detector. The light curtain sensor 2 is disposed downstream of the radiation beam flux plane P1 in the advancing direction of the moving object. Specifically, the light curtain sensor 2 and 3 are disposed at both sides of the radiation beam flux plane P1 near the radiation beam flux plane P1, respectively, as shown in FIGS. 1 and 2. Those skilled in the art can understand that the fourth detector is not limited to the light curtain sensor 2, but may, for example, comprise any appropriate sensors known to the art.

The light curtain sensor 2 has substantially the same function as the light curtain sensor 3, so that detailed description of the light curtain sensor 2 is omitted. It should be noted that the light curtain sensor 2 is provided to further improve the safety and avoid misoperation of the radiation source 7a.

In other words, in an example of the present invention, only when all the light curtain sensor 2, the light curtain sensor 3, the ground induction coil sensor 4, and the photoelectric switch 5 detect the vehicle 1 under inspection in sequence so that they all send positive signals to the controller 8 in sequence, the controller 8 controls the radiation source 7a to automatically emit radiation. If anyone of the light curtain sensor 2, the light curtain sensor 3, the ground induction coil sensor 4, and the photoelectric switch 5 does not send a positive signal to the controller 8, the controller 8 controls the radiation source 7a not to automatically emit radiation, so as to further improve the safety and reliably avoid misoperation of the radiation source 7a.

Figure 3:
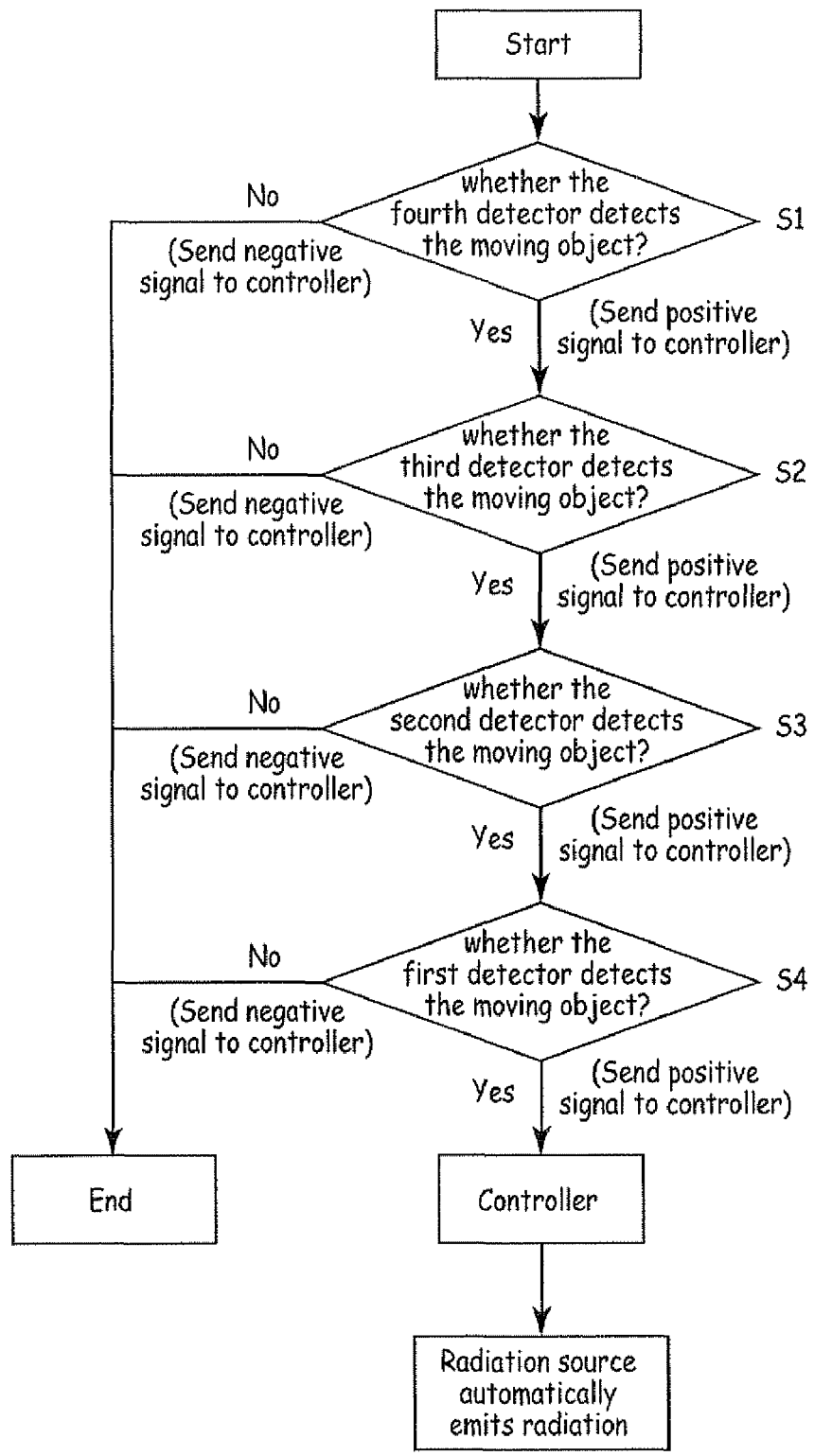
FIG. 3 is a flow diagram of controlling the radiation source to automatically emit a radiation beam according to the embodiment of the present invention.

Referring to FIG. 3, a method for controlling the radiation source 7a by the control unit 100 for controlling the radiation source configured as above according to the present invention is described below. FIG. 3 is a flow diagram of controlling the radiation source 7a according to an embodiment of the present invention. The control unit 100 is provided with the light curtain sensor 2, the light curtain sensor 3, the ground induction coil sensor 4, and the photoelectric switch 5 as the first through fourth detectors.

The vehicle 1 under inspection enters into the inspection passage T from the inlet side (the right sides in FIGS. 1 and 2) of the inspection passage T, and advances towards the outlet side (the left sides in FIGS. 1 and 2) of the inspection passage T.

Firstly, when the vehicle 1 under inspection moves to a position 1A, the light curtain switch 2 detects the vehicle 1 under inspection (step S1). If the light curtain switch 2 detects the vehicle 1 under inspection, then it sends a positive signal to the controller 8. If the light curtain switch 2 does not detect the vehicle 1 under inspection or the vehicle 1 under inspection does not comply with a predetermined standard, then the light curtain switch 2 sends a negative signal to the controller 8 to end the inspection.

Next, the vehicle 1 continues moving forwards so as to pass through the radiation beam flux plane P1. The light curtain switch 3 detects the vehicle 1 under inspection (step S2). If the light curtain switch 3 detects the vehicle 1 under inspection, then it sends a positive signal to the controller 8. If the light curtain switch 3 does not detect the vehicle 1 under inspection or the vehicle 1 under inspection does not comply with a predetermined standard, then the light curtain switch 3 sends a negative signal to the controller 8.

When the vehicle 1 continues moving forwards so as to stand on the ground induction coil sensor 4, the ground induction coil sensor 4 will detect the vehicle 1 under inspection (step S3). If the ground induction coil sensor 4 detects the vehicle 1 under inspection, then the ground induction coil sensor 4 sends a positive signal to the controller 8. If the ground induction coil sensor 4 does not detect the vehicle 1 under inspection, then the ground induction coil sensor 4 sends a negative signal to the controller 8, and the inspection ends.

Thereafter, when the vehicle 1 under inspection moves forwards to a position 1B so that a distance of the cab, which is located at the front portion of the vehicle 1 under inspection, from the radiation beam flux plane P1 reaches a predetermined distance L1, the photoelectric switch 5 detects the vehicle 1 under inspection (step S4). It should be noted that as described above, when the distance of the cab from the radiation beam flux plane P1 reaches the predetermined distance L1, the rear portion, that is, a portion containing cargos to be inspected, of the vehicle 1 under inspection has not yet passed through the radiation beam flux plane P1. If the vehicle 1 under inspection has a height not less than the predetermined height H1, then the photoelectric switch 5 detects the vehicle 1 under inspection so that the photoelectric switch 5 sends a positive signal to the controller 8, and otherwise, the photoelectric switch 5 sends a negative signal to the controller 8 and the inspection ends.

If all the light curtain sensor 2, the light curtain sensor 3, the ground induction coil sensor 4, and the photoelectric switch 5 send positive signals to the controller 8 in sequence, then the controller 8 sends a control signal to the radiation source 7*a*, so that the radiation source 7*a* automatically emits a radiation beam (step S5) for scanning, imaging and inspecting the vehicle 1 under inspection.

It should be noted that in the present invention, the detection of the vehicle 1 under inspection by the light curtain sensor 2, the light curtain sensor 3, the ground induction coil sensor 4, and the photoelectric switch 5 means: (1) the light curtain sensor 2, the light curtain sensor 3, the ground induction coil sensor 4, and the photoelectric switch 5 detect presence of the vehicle 1 under inspection, and (2) the vehicle 1 under inspection detected by the light curtain sensor 2, the light curtain sensor 3, the ground induction coil sensor 4, and the photoelectric switch 5 satisfies predetermined conditions. For example, only when the vehicle 1 under inspection detected by the light curtain sensor 2 and the light curtain sensor 3 matches a predetermined type vehicle, the light curtain sensor 2 and the light curtain sensor 3 send a positive signal to the controller 8. In addition, for example, only when the ground induction coil sensor 4 detects that an area by which the vehicle 1 under inspection overlaps or contacts the ground induction coil sensor 4 satisfies predetermined conditions, the ground induction coil sensor 4 sends a positive signal to the controller 8.

It should be noted that in the above embodiment, the control unit 100 is provided with the light curtain sensor 2, the light curtain sensor 3, the ground induction coil sensor 4, and the photoelectric switch 5 as the first through fourth detectors, but this is only a preferable manner of the present application. Alternatively, the control unit 100 may be provided with only the photoelectric switch 5, or only the ground induction coil sensor 4 and the photoelectric switch 5, or only the light curtain sensor 3, the ground induction coil sensor 4 and the photoelectric switch 5. In any one of the above solutions, the principle for controlling the radiation source 7*a* with the controller 8 is substantially the same. Therefore, only the case in which the control unit 100 is provided with the light curtain sensor 2, the light curtain sensor 3, the ground induction coil sensor 4, and the photoelectric switch 5 is described in detail in the above embodiment, and a detailed description of other cases is omitted.

A radiation inspection system comprising the above control unit 100 and a radiation inspection method thereof are simply described hereinafter.

A radiation inspection system according to an embodiment of the present invention comprises the above control unit 100, an inspection passage T through which a moving object under inspection can pass, a radiation source 7*a* disposed on a side of the inspection passage T for emitting radiation, and an array of detectors 10*a* disposed on the other side of the inspection passage T opposite to the radiation source 7*a* for receiving the radiation emitted from the radiation source 7*a*. Preferably, the an array of detectors 10*a* is disposed on a detector arm 10.

As described above, when all the light curtain sensor 2, the light curtain sensor 3, the ground induction coil sensor 4, and The photoelectric switch 5 as the first through fourth detectors send positive signals to controller 8, the controller 8 controls the radiation source 7*a* to automatically emit a radiation beam. The radiation beam emitted from the radiation source 7*a* is received by the array of detectors 10*a* on the detector arm 10 located on the other side of the inspection passage T, so as to scan, image and inspect goods on the vehicle 1 under inspection as a moving object. As for a device for imaging the goods, it can employ the same imaging device as that in the prior art. The detail description of the imaging device is omitted for purpose of brevity. As an example, the control unit 100 in the above radiation inspection system is provided with the light curtain sensor 2, the light curtain sensor 3, the ground induction coil sensor 4, and the photoelectric switch 5 as the first through fourth detectors, but as described above, this is only a preferable manner of the present application and it is not intended to limit the scope of the present invention.

With the above configuration according to the present invention, detectors for detecting the moving objects are provided, and if the detectors detect moving objects or the detected moving objects satisfy the predetermined conditions by detecting the moving objects with the detectors, then the detectors send positive signals to the controller so that the controller controls the radiation source to automatically emit radiation for inspecting the moving objects. Therefore, the need to manually start the radiation is avoided, the time is saved, and the efficiency is improved. Furthermore, since the controller controls the radiation source to automatically emit the radiation by the detection signals from the detectors, the safety of the system is further improved.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A control unit for controlling a radiation source, wherein the radiation source being operable to emit radiation for inspecting a moving object passing through an inspection passage, the control unit comprising:
   a first detector disposed downstream of the radiation source in an advancing direction of the moving object and spaced from the radiation source by a predetermined distance to detect the moving object passing through the inspection passage
   a second detector disposed under the ground surface of the inspection passage upstream of the first detector in the advancing direction of the moving object, and between the first detector and the radiation source; and
   a controller for receiving signals from the first detector and the second detector,
   wherein only when both the first detector and the second detector detect the moving object, the controller controls the radiation source to automatically emit the radiation;
   wherein the first detector comprises a photoelectric switch, and the second detector comprises a ground induction coil sensor.

2. The control unit according to claim 1, further comprising a third detector disposed upstream of the second detector in the advancing direction of the moving object,
   wherein only when all the third detector, the first detector and the second detector detect the moving object in sequence, the controller controls the radiation source to automatically emit the radiation.

3. The control unit according to claim 2, wherein the third detector is located between the second detector and the radiation source.

4. The control unit according to claim 3, wherein the third detector comprises a light curtain switch.

5. The control unit according to claim 4, further comprising a fourth detector disposed upstream of the third detector in the advancing direction of the moving object,
   wherein only when all the fourth detector, the third detector, the first detector and the second detector detect the moving object in sequence, the controller controls the radiation source to automatically emit the radiation.

6. The control unit according to claim 5, wherein the fourth detector is located upstream of the radiation source in the advancing direction of the moving object.

7. The control unit according to claim 6, wherein the fourth detector comprises a light curtain switch.

8. The control unit according to claim 1, wherein the first detector is spaced from the ground surface by a predetermined height so as to detect only moving objects with the predetermined height.

9. A method of controlling a radiation source, wherein the radiation source being operable to emit radiation for radiation inspection of a moving object passing through an inspection passage, the method comprising steps of:
   providing a first detector downstream of the radiation source in an advancing direction of the moving object at a predetermined distance from the radiation source,
   providing a second detector under the ground surface of the inspection passage upstream of the first detector in the advancing direction of the moving object, and between the first detector and the radiation source;
   providing a controller for receiving signals from the first detector and the second detector to control the radiation source, and
   controlling the radiation source by the controller to automatically emit the radiation only when both the first detector and the second detector detect the moving object;
   wherein the first detector comprises a photoelectric switch, and the second detector comprises a ground induction coil sensor.

10. The method according to claim 9, further comprising steps of:
   providing a third detector upstream of the second detector in the advancing direction of the moving object, and
   controlling the radiation source by the controller to automatically emit the radiation only when all the third detector, the first detector and the second detector detect the moving object in sequence.

11. The method according to claim 10, wherein the third detector is located between the second detector and the radiation source.

12. The method according to claim 11, wherein the third detector comprises a light curtain switch.

13. The method according to claim 12, further comprising steps of:
   providing a fourth detector upstream of the third detector in the advancing direction of the moving object, and
   controlling the radiation source by the controller to automatically emit the radiation only when all the fourth detector, the third detector, the first detector and the second detector detect the moving object in sequence.

14. The method according to claim 13, wherein the fourth detector is disposed upstream of the radiation source in the advancing direction of the moving object.

15. The method according to claim 14, wherein the fourth detector comprises a light curtain switch.

16. The method according to claim 15, wherein the first detector is spaced from the ground surface by a predetermined height so as to detect only moving objects with the predetermined height.

17. A radiation inspection system, comprising:
   an inspection passage through which a moving object under inspection can pass,
   a radiation source disposed on a side of the inspection passage for emitting radiation,
   an array of detectors disposed on the other side of the inspection passage opposite to the radiation source for receiving the radiation emitted from the radiation source,
   a first detector disposed downstream of the radiation source in an advancing direction of the moving object and spaced from the radiation source by a predetermined distance to detect the moving object,
   a second detector disposed under the ground surface of the inspection passage upstream of the first detector in the advancing direction of the moving object, and between the first detector and the radiation source;
   a controller for receiving signals from the first detector and the second detector,
   wherein only when both the first detector and the second detector detect the moving object, the controller controls the radiation source to automatically emit the radiation for imaging and inspection of the moving object; and
   wherein the first detector comprises a photoelectric switch, and the second detector comprises a ground induction coil sensor.

18. The radiation inspection system according to claim 17, further comprising a third detector disposed upstream of the second detector in the advancing direction of the moving object,
   wherein only when all the third detector, the first detector and the second detector detect the moving object in sequence, the controller controls the radiation source to automatically emit the radiation.

19. The radiation inspection system according to claim 18, wherein the third detector is located between the second detector and the radiation source.

20. The radiation inspection system according to claim 19, wherein the third detector comprises a light curtain switch.

21. The radiation inspection system according to claim 20, further comprising a fourth detector disposed upstream of the third detector in the advancing direction of the moving object,
   wherein only when all the fourth detector, the third detector, the first detector and the second detector detect the moving object in sequence, the controller controls the radiation source to automatically emit the radiation.

22. The radiation inspection system according to claim 21, wherein the fourth detector is located upstream of the radiation source in the advancing direction of the moving object.

23. The radiation inspection system according to claim 22, wherein the fourth detector comprises a light curtain switch.

24. The radiation inspection system according to claim 23, wherein the first detector is spaced from the ground surface by a predetermined height so as to detect only moving objects with the predetermined height.

25. A method of inspecting a moving object with radiation, comprising steps of:
   providing an inspection passage through which the moving object under inspection passes,
   providing a radiation source on a side of the inspection passage for emitting radiation,
   providing an array of detectors on the other side of the inspection passage opposite to the radiation source for receiving the radiation emitted from the radiation source,
   providing a first detector downstream of the radiation source in an advancing direction of the moving object at a predetermined distance from the radiation source,
   providing a second detector under the ground surface of the inspection passage upstream of the first detector in the advancing direction of the moving object, and between the first detector and the radiation source;

providing a controller for receiving signals from the first detector and the second detector so as to control the radiation source, controlling the radiation source by the controller to automatically emit the radiation only when both the first detector and the second detector detect the moving object; and wherein the first detector comprises a photoelectric switch, and the second detector comprises a ground induction coil sensor.

26. The method according to claim 25, further comprising steps of:

providing a third detector upstream of the second detector in the advancing direction of the moving object, and controlling the radiation source by the controller to automatically emit the radiation only when all the third detector, the first detector and the second detector detect the moving object in sequence.

27. The method according to claim 26, wherein the third detector is located between the second detector and the radiation source.

28. The method according to claim 27, wherein the third detector comprises a light curtain switch.

29. The method according to claim 28, further comprising steps of:

providing a fourth detector upstream of the third detector in the advancing direction of the moving object, and controlling the radiation source by the controller to automatically emit the radiation only when all the fourth detector, the third detector, the first detector and the second detector detect the moving object in sequence.

30. The method according to claim 29, wherein the fourth detector is disposed upstream of the radiation source in the advancing direction of the moving object.

31. The method according to claim 30, wherein the fourth detector comprises a light curtain switch.

32. The method according to claim 31, wherein the first detector is spaced from the ground surface by a predetermined height so as to detect only moving objects with the predetermined height.

* * * * *